United States Patent [19]

Sabahi

[11] Patent Number: 5,290,465
[45] Date of Patent: Mar. 1, 1994

[54] NEOPOLYOL DERIVATIVES AND REFRIGERANT COMPOSITIONS COMPRISING THEM

[75] Inventor: Mahmood Sabahi, Baton Rouge, La.

[73] Assignee: Ethyl Corporation, Richmond, Va.

[21] Appl. No.: 887,988

[22] Filed: May 22, 1992

Related U.S. Application Data

[63] Continuation-in-part of Ser. No. 663,620, Mar. 4, 1991, abandoned.

[51] Int. Cl.$^5$ .............. C10M 105/02; C09K 5/00; C07C 69/66
[52] U.S. Cl. ..................... 252/56 R; 252/68; 252/56 S; 560/187
[58] Field of Search ............ 252/56 R, 67, 68, 56 S; 560/187

[56] References Cited

U.S. PATENT DOCUMENTS

| | | | |
|---|---|---|---|
| 2,936,856 | 5/1960 | Braunwarth et al. | 184/109 |
| 3,770,808 | 11/1973 | Marquis et al. | 560/187 |
| 4,159,255 | 6/1979 | Gainer et al. | 252/52 R |
| 4,267,064 | 5/1981 | Sasaki et al. | 252/52 A |
| 4,423,071 | 12/1983 | Chignac et al. | 560/187 |
| 4,945,179 | 7/1990 | Drent | 560/187 |
| 4,948,915 | 8/1990 | Keen | 560/187 |
| 5,011,977 | 4/1991 | Jones et al. | 560/187 |
| 5,021,179 | 6/1991 | Zehler et al. | 252/54.6 |

FOREIGN PATENT DOCUMENTS

| | | |
|---|---|---|
| 3925256 | 1/1991 | Fed. Rep. of Germany . |
| 59-167537 | 9/1984 | Japan . |
| 90/06979 | 6/1990 | World Int. Prop. O. . |

OTHER PUBLICATIONS

Macromolecules, vol. 24, #6, Newkome et al, "Symmetrical, Four-Directional, Poly(Ether-Amide) Cascade Polymers" Mar. 18, 1991.

*Primary Examiner*—Prince Willis, Jr.
*Assistant Examiner*—J. Silbermann
*Attorney, Agent, or Firm*—Patricia J. Hogan

[57] ABSTRACT

Neopolyol derivatives in which at least one of the hydroxyl groups is replaced with a substituent that corresponds to the formula —O—R—C(O)—OR' wherein R is an alkylene group containing 2-5 carbons and R' is a hydrocarbyl or predominantly hydrocarbyl group containing 1-30 carbons are oils which have utility as lubricants. Those in which R' is a hydrocarbyl group of 1-10 carbons are completely miscible with 1,1,1,2-tetrafluoroethane (R-134a), a refrigerant.

12 Claims, No Drawings

NEOPOLYOL DERIVATIVES AND REFRIGERANT COMPOSITIONS COMPRISING THEM

CROSS-REFERENCE TO RELATED APPLICATION

This application is a continuation-in-part of copending application Ser. No. 07/663,620, filed Mar. 4, 1991 now abandoned.

FIELD OF INVENTION

The invention relates to neopolyol derivatives and more particularly to such compounds having utility as lubricants.

BACKGROUND

Many natural and synthetic materials are known to be useful as lubricants, their utility in particular applications depending on factors such as their stability and viscosity under the conditions of use, their pour points, and their compatibility with any materials with which they will be used.

In refrigeration applications (e.g., home-use or industrial-use refrigerators, freezers, or air conditioners for buildings, automobiles, airplanes, and other vehicles), mineral oils have usually been the lubricants of choice in the past since—in addition to being inexpensive and having other desirable properties—they are compatible with the chlorofluorocarbons that have most commonly been employed as refrigerants. However, mineral oils are incompatible with 1,1,1,2-tetrafluoroethane (R-134a), a refrigerant which has been reported to have an ozone depletion potential of zero and has therefore been proposed as a replacement for the chlorofluorocarbons believed to be depleting the earth's ozone layer, e.g., chlorotrifluoromethane (R-11), dichlorodifluoromethane (R-12), and 1,2,2-trifluoro-1,1,2-trichloroethane (R-113).

PCT Application WO 90/06979 (Jolley et al.), published Jun. 28, 1990, discloses several carboxylic esters which are said to be useful as lubricants for R-134a and other halohydrocarbon refrigerants; and U.S. Pat. No. 5,021,179 (Zehler et al.) teaches certain polyhydric alcohol esters, including pentaerythritol esters, to be effective lubricants for R-134a and other fluorocarbon refrigerants.

U.S. Pat. No. 4,159,255 (Gainer et al.) discloses the use of some castor oil/neopolyol ester blends as refrigeration lubricants, while U.S. Pat. No. 4,267,064 (Sasaki et al.) teaches other such lubricants which correspond to the formula $R_1[-O-(R_2O)_m-R_3]_n$ and may be derived from a neopolyol or other monohydric or polyhydric alcohol. Other synthetic lubricants which can be obtained from neopolyols are some of the esters of U.S. Pat. No. 3,770,808 (Marquis et al.).

SUMMARY OF INVENTION

The invention resides in (1) novel substituted neopolyols in which at least one of the hydroxyl groups is replaced with a substituent that corresponds to the formula:

—O—R—C(O)—OR' wherein R is an alkylene group containing 2-5 carbons and R' is a hydrocarbyl or predominantly hydrocarbyl group containing 1-30 carbons, (2) processes for preparing them, and (3) their uses as lubricants, especially refrigeration lubricants.

DETAILED DESCRIPTION

The compounds of the invention are ether-esters which are derived from neopolyols, i.e., polyhydric alcohols containing at least one quaternary carbon, and they may be prepared by reacting the neopolyol with an $\alpha,\beta$-unsaturated nitrile and then hydrolyzing and esterifying the intermediate nitrile to form an ester.

The neopolyol starting material may be any polyhydric alcohol containing at least one quaternary carbon, e.g., pentaerythritol, dipentaerythritol, trimethylolethane, trimethylolpropane, or neopentyl glycol.

The unsaturated nitrile with which the neopolyol is reacted is a compound corresponding to the formula TCH=C(T')CN wherein T and T' are independently selected from hydrogen and alkyl so that the —C(T)H—C(T')H— group into which the TCH=C(T')— group is converted by the reaction is the desired —R— alkylene group of the above formula, i.e., an alkylene group of 2-5 carbons, preferably 2-3 carbons. Such compounds include, e.g., nitriles such as acrylonitrile, methacrylonitrile, ethacrylonitrile, vinyl acetonitrile, vinyl propionitrile, and vinyl butyronitrile.

In the preparation of the compounds of the invention, (1) the neopolyol is reacted with an amount of TCH=C(T')CN unsaturated nitrile sufficient to replace the desired number of —OH groups of the neopolyol with —ORCN groups, employing conventional techniques, such as the use of a dioxane or other ether solvent, a basic catalyst such as potassium hydroxide, and temperatures of 20°–50° C., and (2) the resultant intermediate is then simultaneously hydrolyzed and esterified with a suitable reagent, such as an alkanol, cycloalkanol, aralkanol, or phenol corresponding to the formula R'OH, to form the ester or a mixture thereof with the primary amide and possibly also with a minor amount of a secondary amide having an —O—R—C(O)—NHR' group corresponding to the —O—R—C(O)—OR' group of the ester.

Exemplary of the R'OH reagents which may be used in the reaction are those in which R' is methyl, ethyl, propyl, hexyl, decyl, dodecyl, octadecyl, eicosyl, tetracosyl, triacontyl, hydroxydodecyl, ethoxydecyl, propoxyoctadecyl, 6-aminohexyl, cyclohexyl, phenyl, tolyl, and phenethyl.

As indicated by the examples of groups that may constitute R', these groups are at least predominantly hydrocarbyl in nature, but they may contain atoms other than carbon and hydrogen. These other atoms may be hetero atoms, such as oxygen, sulfur, or phosphorus atoms, which are part of an R' chain or ring; or they may be present in substituent groups, such as hydroxy, amino, halo, or cyano groups. However, to preserve the predominantly hydrocarbyl nature of R', the number of hetero atoms or non-hydrocarbyl substituents in the group should not exceed 0.3 per carbon and is preferably not more than 0.1 per carbon. Halo substituents are apt to be undesirable when the products are to be used as refrigeration lubricants, and hydrocarbyl R' groups are generally preferred.

Although the by-products containing —O—R—C(O)—NH₂ and —O—R—C(O)—NHR' groups do not appear to have an adverse effect on the performance of the ether-esters of the invention, it is usually preferred for the novel compounds to be prepared by a process

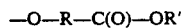

which results in the formation of not more than 50%, preferably not more than 30% by weight of by-products in the final product.

In a preferred embodiment of the invention, the novel ether-esters are prepared by reacting an intermediate nitrile corresponding to the formula R"(—ORCN)$_n$ in which R" is the neopolyol residue and n is an integer of at least one, preferably an integer equivalent to the number of hydroxyl groups originally present in the neopolyol, with at least stoichiometric amounts of water and a suitable esterifying agent in the presence of a strongly acidic catalyst, such as hydrochloric or sulfuric acid, at a suitable temperature, e.g., 20°-80° C., to form an ester containing a minimum amount of amide. However, it may sometimes be desirable—at least when the catalyst is a strong acid other than hydrochloric acid—to use temperatures higher than 20°-80° C., e.g., temperatures as high as 150°-200° C.

The ether-esters of the invention are oils which are useful as lubricants in a variety of applications, depending on their particular viscosities and their degrees of compatibility with any materials with which they will be used. When they are to be utilized as refrigeration lubricants, (1) those in which R' is a hydrocarbyl group of 1-10 carbons have such good miscibility with R-134a that they are of particular interest as lubricants for use with that refrigerant, although they are also useful in conjunction with other refrigerants, such as chlorofluorocarbons, while (2) the compounds containing larger R' groups have their utility as lubricants for use with those other refrigerants, e.g., chlorofluorocarbons. Among the ether-esters which appear to be primarily of interest as lubricants for use with R-134a, one of the preferred compounds is a tetra(butylcarboxyethyl) ether of pentaerythritol containing minor amounts of amide by-products and having a viscosity of 10.2-31.2 cSt (10.2-31.2 mm$^2$.s$^{-1}$) at 40° C. with good lubricity.

When used as refrigeration lubricants, the ether-esters have sufficient compatibility with halohydrocarbon refrigerants to be used at the generally-desired concentrations of 5-15% by weight at temperatures of −40° C. to 80° C.—the temperatures at which compatibility is normally tested for refrigeration compositions. Most commonly, the lubricants are used in amounts such as to provide refrigerant/lubricant weight ratios of 3-20/1, preferably about 10/1; and the refrigerant with which they are used is a chlorofluorocarbon such as chlorotrifluoromethane, dichlorodifluoromethane, dichlorofluoromethane, chlorodifluoromethane, 1,2,2-trifluoro-1,1,2-trichloroethane, 1,1-dichloro-2,2,2-trifluoroethane, 1,1-dichloro-1-fluoroethane, 1-chloro-2,2,2-trifluoroethane, or 1-chloro-1,1,2,2-tetrafluoroethane; dichloromethane; or, more preferably, a fluorocarbon such as 1,1,2,2-tetrafluoroethane (R-134) or 1,1,1,2-tetrafluoroethane (R-134a).

The most preferred refrigeration lubricants of the invention are the ether-esters which are substituted neopolyols in which all, or substantially all, of the hydroxyl groups are replaced with a substituent that corresponds to the formula —O—(CH$_2$)$_n$—C(O)—OR' in which n is two or three and R' is an alkyl group of 1-10 carbons, preferably 6-8 carbons.

When used, these preferred lubricants, as well as the other lubricants of the invention, may be used in conjunction with additives of the type conventionally used in refrigeration lubricants. Such additives include, e.g., oxidation resistance and thermal stability improvers, corrosion inhibitors, metal deactivators, lubricity additives, viscosity index improvers, pour and/or floc point depressants, detergents, dispersants, antifoaming agents, anti-wear agents, and extreme pressure resistance additives, such as those exemplified in Zehler et al., the teachings of which are incorporated herein by reference. As in Zehler et al., these additives, when employed, are generally utilized in small amounts totaling not more than 8%, preferably not more than 5%, of the weight of the lubricant formulation.

If desired, the lubricants of the invention may also be used in conjunction with known lubricants, preferably in such amounts that the novel lubricants constitute at least 50%, more preferably at least 70% of the weight of the composition.

The following examples are given to illustrate the invention and are not intended as a limitation thereof. Unless otherwise specified, quantities mentioned in the examples are quantities by weight.

EXAMPLE 1

Preparation of Tetra(butylcarboxyethyl)ether of Pentaerythritol

Part A

Sequentially add 0.1 g of 40% potassium hydroxide and 4.6 g (0.087 mol) of acrylonitrile to a suspension of 2.4 g (0.018 mol) of pentaerythritol in 20 mL of 1,4-dioxane at room temperature with stirring. Warm the reaction mixture to ∼50° C., stir at this temperature for two hours, cool to room temperature and stir overnight. Then neutralize the solution with hydrochloric acid, remove the solvent under reduced pressure, dissolve the remaining oil in dichloromethane, dry over magnesium sulfate, evaporate the solvent under reduced pressure to provide a viscous oil, and further purify the viscous oil over neutral alumina. Chromatographic analysis shows the product to be the tetra(cyanoethyl) ether of pentaerythritol (TCEP).

Part B

Add 4.3 g (0.24 mol) of water to a suspension of 21.0 g (0.06 mol) of TCEP in 120 mL of n-butanol and then introduce 17.5 g (0.48 mol) of HCl gas at room temperature. Stir the cloudy reaction mixture at room temperature overnight, heat gently to ∼80° C., and maintain this temperature for three hours. Add water to dissolve the heavy white solid, separate the organic phase, and extract the aqueous phase with dichloromethane (4×25 mL). Wash the combined organic extract with water (2×30 mL) and saturated sodium bicarbonate solution, dry over magnesium sulfate, evaporate the residual alcohol under reduced pressure, and distill at 130° C. and 0.13-0.15 mm Hg to remove the volatiles. Spectroscopic analysis shows the remaining oily residue to be mainly the tetra(butylcarboxyethyl) ether of pentaerythritol.

EXAMPLE 2

Preparation of Other Pentaerythritol Ether-Esters

Prepare three other ether-esters by the procedure of Example 1, Part B, except for replacing the n-butanol with, respectively:
(a) n-hexanol,
(b) a mixture of 47.2% dodecanol, 20.2% tetradecanol, 9.4% hexadecanol, 8.2% decanol, 7.6% octadecanol, 6.8% octanol, 0.5% hexanol, and 0.1% eicosanol, and (c) a mixture of 66.3% dodecanol, 26.6% tetradecanol, and 7.1% hexadecanol.

Each of the products is mainly a tetra(alkylcarboxyethyl) ether, or a mixture of tetra(alkylcarboxyethyl) ethers, of pentaerythritol in which the alkyl groups are those derived from the alcohol or alcohols employed.

EXAMPLE 3

Preparation of Di(butylcarboxyethyl)ether of Neopentyl Glycol

React a slight excess of acrylonitrile with neopentyl glycol by the general procedure of Example 1, Part A, to form the di(cyanoethyl) ether of the glycol. Then prepare an oil by reacting that ether with water and n-butanol in the presence of HCl, using essentially the same procedure as in Example 1, Part B. Spectroscopic analysis shows the residue after workup to be mainly the di(butylcarboxyethyl)ether of neopentyl glycol.

EXAMPLE 4

Preparation of Dipentaerythritol Ether-Esters

Part A

Charge a suitable reaction vessel with 5.72 g (0.01 mol) of the hexa(cyanoethyl) ether of dipentaerythritol, 50 mL of n-butanol, and 1.08 mL (0.06 mol) of water, and then introduce 4.5 g (0.12 mol) of HCl gas. Warm the reaction mixture to 50° C., stir at this temperature overnight, then warm to 80° C., and stir for two hours at this higher temperature. After adding water, separate the organic phase and wash it with water and sodium bicarbonate until neutral. Then dry it over magnesium sulfate, filter, and evaporate under reduced pressure to remove residual alcohol and the remaining volatiles. Spectroscopic analysis shows the residue to be mainly the hexa(butylcarboxyethyl) ether of dipentaerythritol with minor amounts of amidocarboxyethyl ethers of dipentaerythritol.

Part B

Repeat Part A except for replacing the butanol with ethanol. Similar results are observed, except that the product is mainly the hexa(ethylcarboxyethyl) ether of dipentaerythritol.

EXAMPLE 5

Miscibility Studies

Test the miscibility of the ether-esters of Examples 1, 2b, and 3 with R-134a by sealing 4/1 mixtures of the refrigerant and ether-ester in pyrex tubes and generating phase diagrams for the mixtures from −50° C. to 70° C.—the maintenance of a single phase indicating complete miscibility, and separation into two phases indicating immiscibility. The test shows that the ether-esters of Examples 1 and 3, which have four carbons in the esterifying groups, are completely miscible with R-134a throughout the temperature range of the test, but the ether-ester of Example 2b, in which more than 80% of the esterifying groups contain more than 10 carbons, is immiscible with the refrigerant.

What is claimed is:

1. A substituted neopolyol which is selected from the group consisting of pentaerythritol, dipentaerythritol, trimethylolethane, and trimethylolpropane and in which at least one of the hydroxyl groups is replaced with a substituent that corresponds to the formula —O—R—C(O)—OR' wherein R is an alkylene group containing 2-5 carbons and R' is an alkyl group containing 1-30 carbons.

2. The substituted neopolyol of claim 1 wherein at least substantially all of the hydroxyl groups are replaced with a substituent that corresponds to the formula:

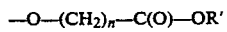

in which n is two or three and R' is an alkyl group of 1-10 carbons.

3. The substituted neopolyol of claim 2 wherein the neopolyol is pentaerythritol.

4. The substituted neopolyol of claim 2 wherein the neopolyol is dipentaerythritol.

5. A refrigeration composition which comprises 3-20 parts by weight of a halohydrocarbon refrigerant and one part by weight of a substituted neopolyol lubricant in which at least one of the hydroxyl groups is replaced with a substitutent that corresponds to the formula —O—R—C(O)—OR' wherein R is an alkylene group containing 2-5 carbons and R' is a hydrocarbyl or predominantly hydrocarbyl group containing 1-30 carbons.

6. The refrigeration composition of claim 5 wherein the refrigerant/lubricant weight ratio is about 10.

7. The refrigeration composition of claim 5 wherein the neopolyol is pentaerythritol, dipentaerythritol, trimethylolethane, trimethylolpropane, or neopentyl glycol.

8. The refrigeration composition of claim 5 wherein the halohydrocarbon refrigerant is 1,1,1,2-tetrafluoroethane.

9. The refrigeration composition of claim 16 wherein at least substantially all of the hydroxyl groups of the neopolyol are replaced with a substituent that corresponds to the formula —O—(CH$_2$)$_n$—C(O)—OR' in which n is two or three and R' is an alkyl group of 1-10 carbons.

10. The refrigeration composition of claim 9 wherein the neopolyol is pentaerythritol.

11. The refrigeration composition of claim 9 wherein the neopolyol is dipentaerythritol.

12. The refrigeration composition of claim 9 wherein the neopolyol is neopentyl glycol.

* * * * *